US00PP32718P2

(12) United States Plant Patent
NeSmith

(10) Patent No.: US PP32,718 P2
(45) Date of Patent: Jan. 5, 2021

(54) SOUTHERN HIGHBUSH BLUEBERRY PLANT NAMED 'TH-1334'

(50) Latin Name: *Vaccinium corymbosum*
Varietal Denomination: TH-1334

(71) Applicant: University of Georgia Research Foundation, Inc., Athens, GA (US)

(72) Inventor: D. Scott NeSmith, Griffin, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 16/602,610

(22) Filed: Nov. 7, 2019

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
CPC ..... A01H 6/368; A01H 5/08
See application file for complete search history.

(56) References Cited

PUBLICATIONS

Top Fruit,http://www.topfruit.co.za/wp-content/uploads/2019/08/Early-Duchess-TH-1334.pdf, obtained from internet May 19, 2020.*

* cited by examiner

*Primary Examiner* — Keith O. Robinson
(74) *Attorney, Agent, or Firm* — Klarquist Sparkman, LLP

(57) ABSTRACT

The new variety 'TH-1334' ripens around mid-April in southeastern Georgia. The fruit of the new variety 'TH-1334' are very large, firm, have good flavor and scar. The new variety 'TH-1334' is vigorous with an estimated chilling requirement of about 50 to 100 hours at or below approximately 7° C. The asexually reproduced variety is reliably propagated vegetatively.

7 Drawing Sheets

STATEMENT REGARDING FEDERALLY-SPONSORED RESEARCH

This invention was made, in part, with U.S. Government support on behalf of U.S. Department of Agriculture, Hatch Act Grant No. GEO 01663. The U.S. Government has certain rights in this invention.

Latin name of the genus and species of the plant claimed: 'TH-1334' is a southern highbush blueberry plant that is a *Vaccinium corymbosum.*

Variety denomination: The new southern highbush blueberry plant claimed is of the variety denominated 'TH-1334'.

BACKGROUND OF THE INVENTION

The present invention relates to the discovery of a new and distinct cultivar of southern highbush blueberry plant botanically known as a *Vaccinium corymbosum* and herein referred to as 'TH-1334', as herein described and illustrated.

The new blueberry plant variety 'TH-1334' was selected in Griffin, Ga. in 2010. The new variety 'TH-1334' is very early season, and begins ripening in South Georgia before the early varieties of 'TH-819' (U.S. Plant Pat. No. 24,696) and 'Rebel' (U.S. Plant Pat. No. 18,138). The fruit of the new variety 'TH-1334' are large with favorable firmness and good flavor. The new variety 'TH-1334' has acceptable yield and is vigorous with an estimated chilling requirement of about 50-100 hours at or below 45° F. when produced under typical low to mid chill production regions.

Pedigree and history: 'TH-1334' was selected in 2010 at Griffin, Ga., originating from a cross of 'TH-639' (female parent, non-patented breeding selection) X 'Rebel' (male parent, U.S. Plant Pat. No. 18,138) made in 2007 by D. Scott NeSmith. 'TH-1334' was asexually propagated by vegetative stem cuttings and tested in plantings at a blueberry research farm in Alapaha, Ga. in 2011.

Observations in plants of the 'TH-1334' variety have shown that the unique features of this new *Vaccinium corymbosum* 'TH-1334' are stable and have reproduced true to type in successive generations.

SUMMARY OF THE INVENTION

The new blueberry plant variety 'TH-1334' has not been observed under all possible environmental conditions. The phenotype may vary somewhat with variations in environment and cultural practices, such as temperature and light intensity, without, however, any variance in genotype.

The following traits have been repeatedly observed in Alapaha, Ga., and are determined to be the unique characteristics of the new blueberry plant variety 'TH-1334':

1. Large berry size;
2. Good berry flavor;
3. Favorable berry firmness; and
4. Very early fruit ripening.

The new variety 'TH-1334' can be compared to the southern highbush blueberry varieties 'TH-819' and 'Rebel'.

Comparison: The selection ripens before 'TH-819' and 'Rebel' in the early Georgia southern highbush season. 'TH-1334' has large, firm berries with good flavor as compared to 'TH-819' and 'Rebel' at Alapaha, Ga. over a 3-year period (Table 1). The female parent, 'TH-639', is an older breeding selection that no longer exists. However, comparing past performances of 'TH-1334' to 'TH-639' demonstrated they both have similar chilling requirements of 50 to 100 hours below 45 F. 'TH-639' berries had smaller berry size, weighing 2.5 to 3.0 g at first harvest and having berry diameters of 16 to 18 mm, compared to weights of 3.0 g to 3.8 g and diameters of 17 to 21 mm for 'TH-1334'. 'TH-639' had better berry color, averaging 8.0 to 8.5 on a scale of 1 to 10, compared to an average of 7.0 for 'TH-1334'. 'TH-639' had an average plant vigor score of 7.5 compared to the score of 8.0 for 'TH-1334'. Flowering dates and ripening dates averaged similarly for the two varieties.

TABLE 1

Table 1 sets forth three-year average ratings of some fruit and plant characteristics of 'TH-1334' and standard cultivars 'TH-819' and 'Rebel' from 2014-2016 in field test plots at Alapaha, GA.

| | 'TH-819' | 'Rebel' | 'TH-1334' |
|---|---|---|---|
| Berry size | 7.2 | 7.7 | 8.6 |
| Berry scar | 7.3 | 7.5 | 7.4 |
| Berry color | 7.0 | 7.4 | 7.0 |
| Berry firmness | 7.0 | 7.5 | 7.8 |
| Berry flavor | 8.0 | 6.5 | 7.3 |
| Cropping | 3.4 | 6.0 | 2.0 |
| Plant vigor | 8.5 | 7.5 | 8.0 |
| Date of 50% flowering | Feb. 16 | Feb. 27 | Feb. 7 |
| Date of 50% ripening | April 24 | April 30 | April 15 |
| Fruit development period (days) | 67 | 62 | 67 |

Rating scales are based on a 1 to 10 score, with 1 being the least desirable and 10 being the most desirable. A value of 6-7 is generally considered to be the minimum acceptable rating for a commercial cultivar. These plants were established in 2011.

BRIEF DESCRIPTION OF THE DRAWINGS

The accompanying photographic illustrations show typical specimens in full color of the foliage, flowering, and fruit of the new variety 'TH-1334'. The colors are as nearly true as is reasonably possible in a color representation of this type. The age of the plants depicted in the photographs is between 6 and seven years old. The observations for 'TH-1334' presented here have only been made in a temperate climate. Therefore, dormancy occurs and fruiting is only on one year old shoots. The environment is not conducive to seeing flowering and fruiting on current season shoots.

DETAILED BOTANICAL DESCRIPTION

Figure 1:
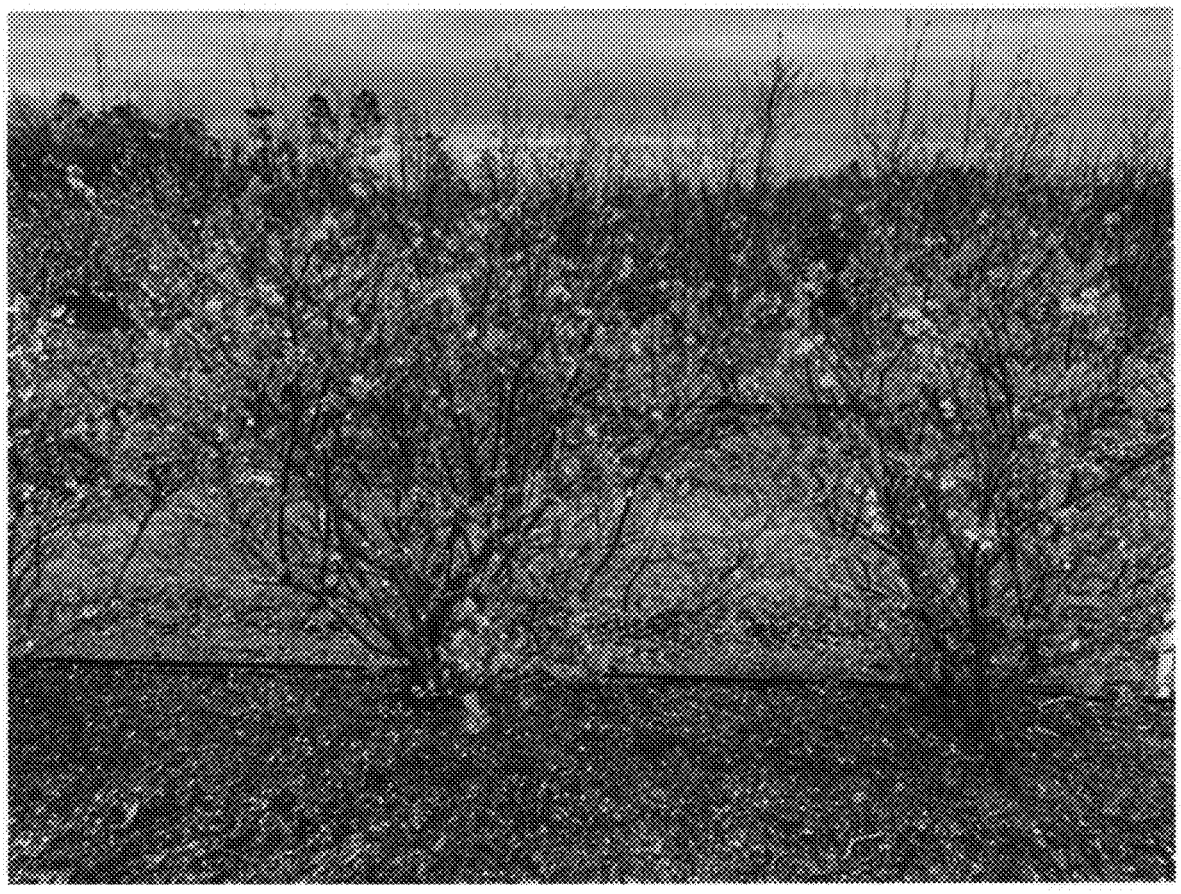
FIG. 1 is a photograph of plants of the new variety 'TH-1334' during flowering at Alapaha, Ga.
Figure 2:
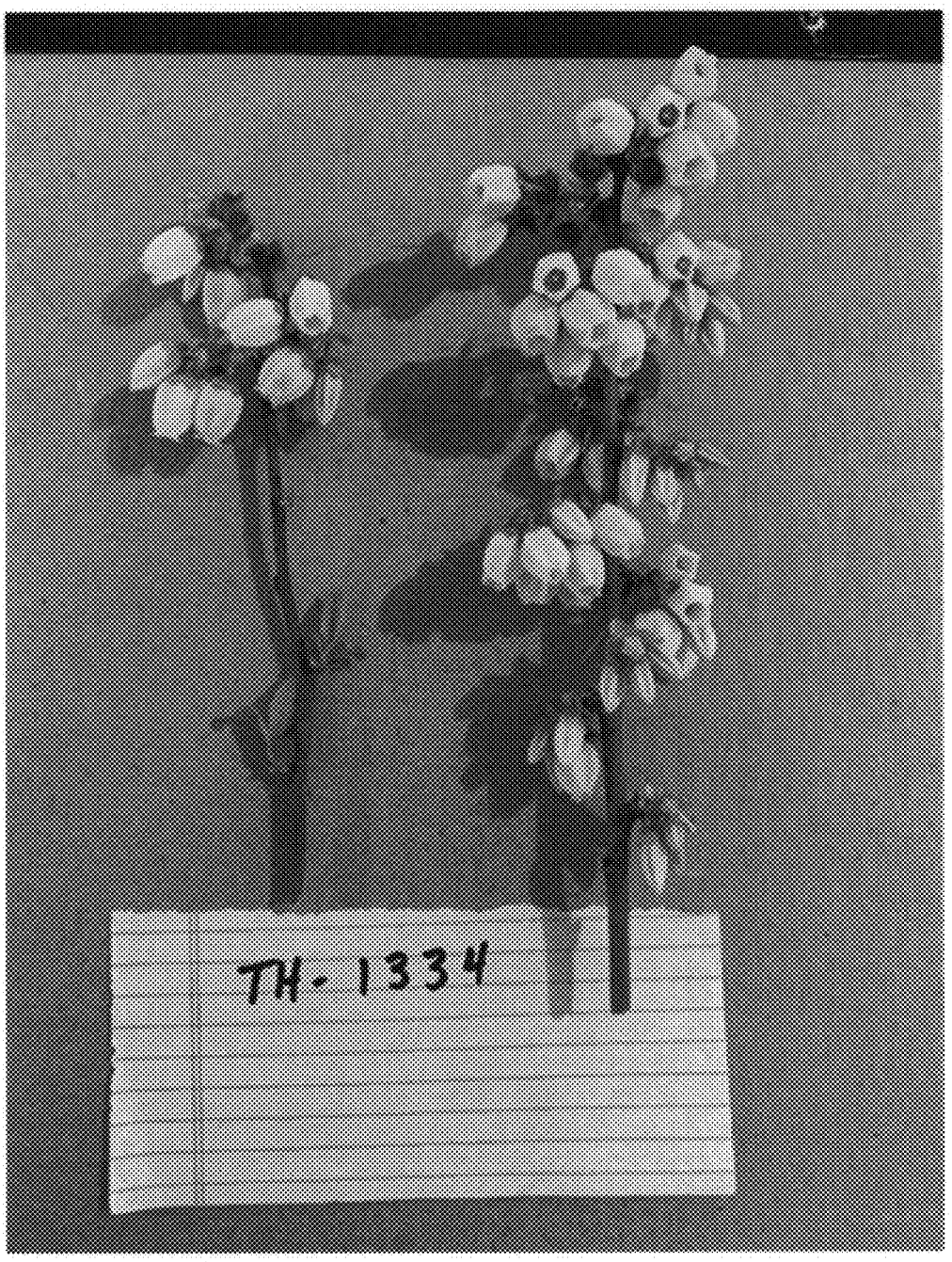
FIG. 2 is a close up photograph of the flowers of the new variety 'TH-1334' at Alapaha, Ga.
Figure 3:
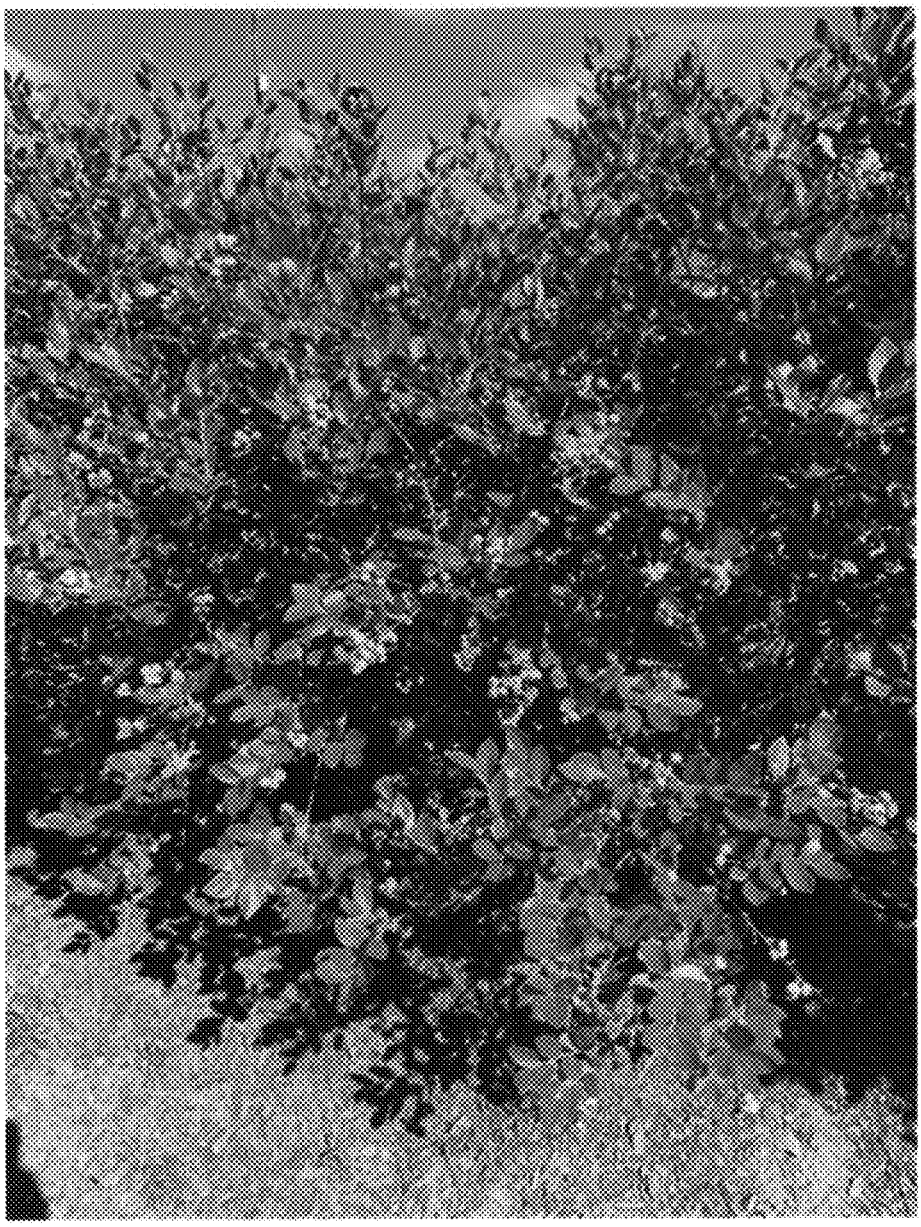
FIG. 3 is a photograph of mature plants of 'TH-1334' during ripening at Alapaha, Ga.
Figure 4:
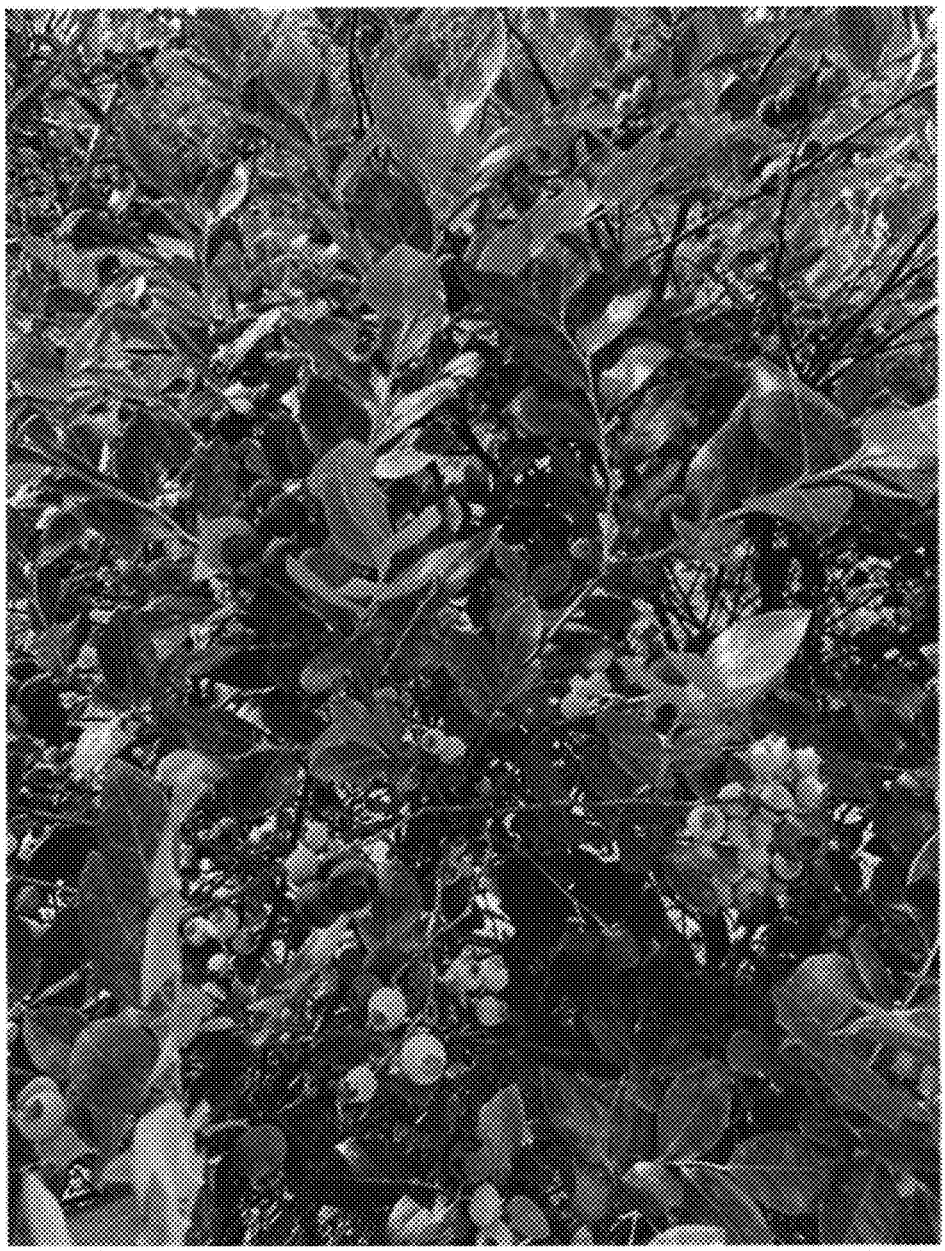
FIG. 4 is a close up photograph of the 'TH-1334' fruit as it matures at Alapaha, Ga.
Figure 5:
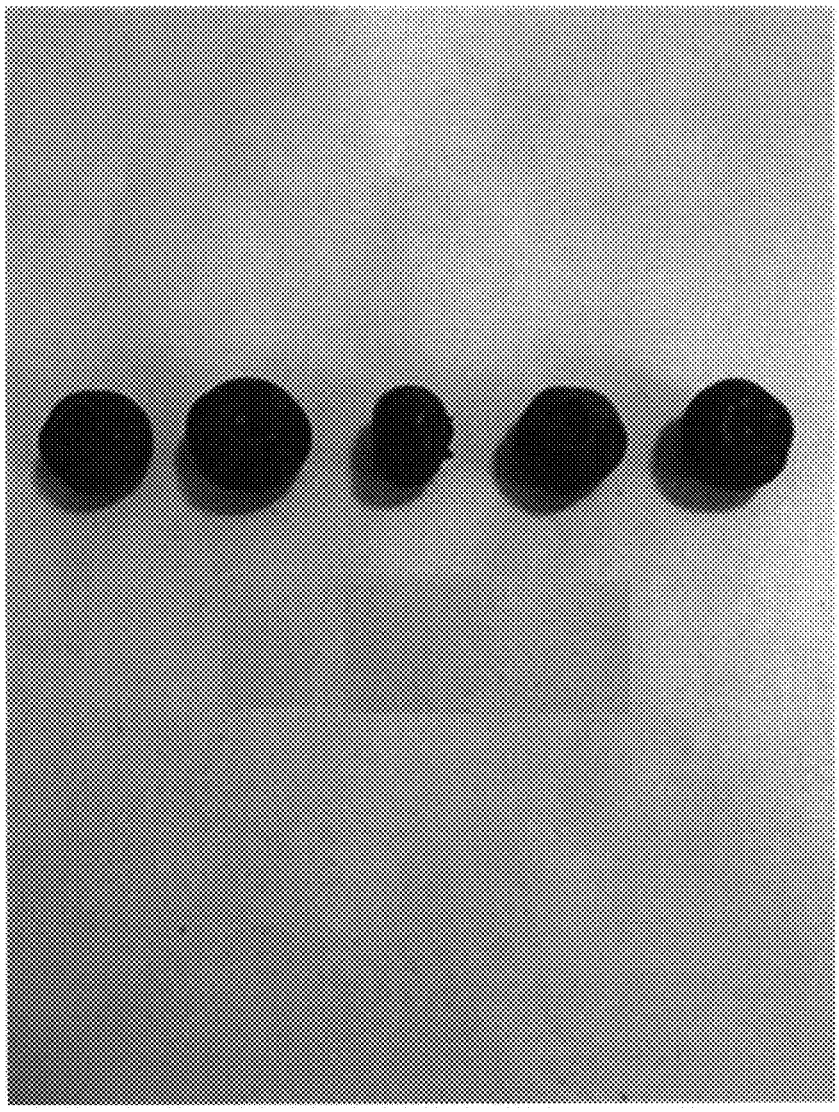
FIGS. 5, 6 and 7 are photographs of the 'TH-1334' fruit.
Figure 6:
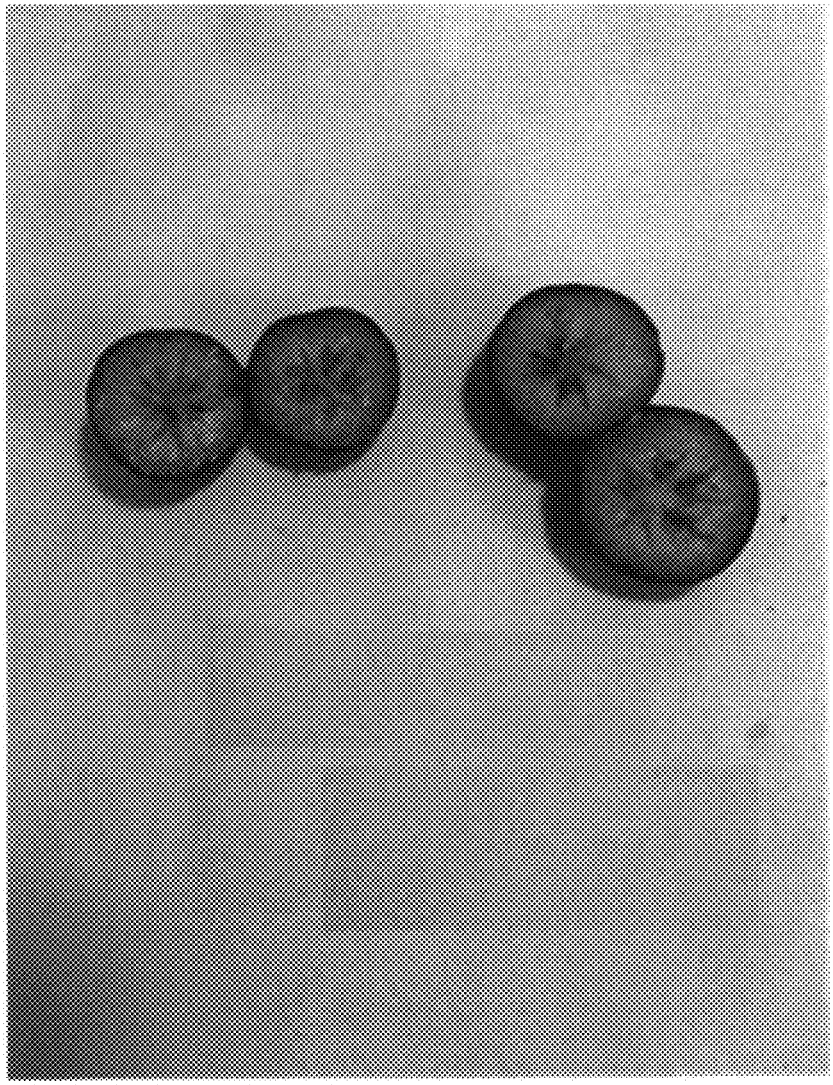
Figure 7:
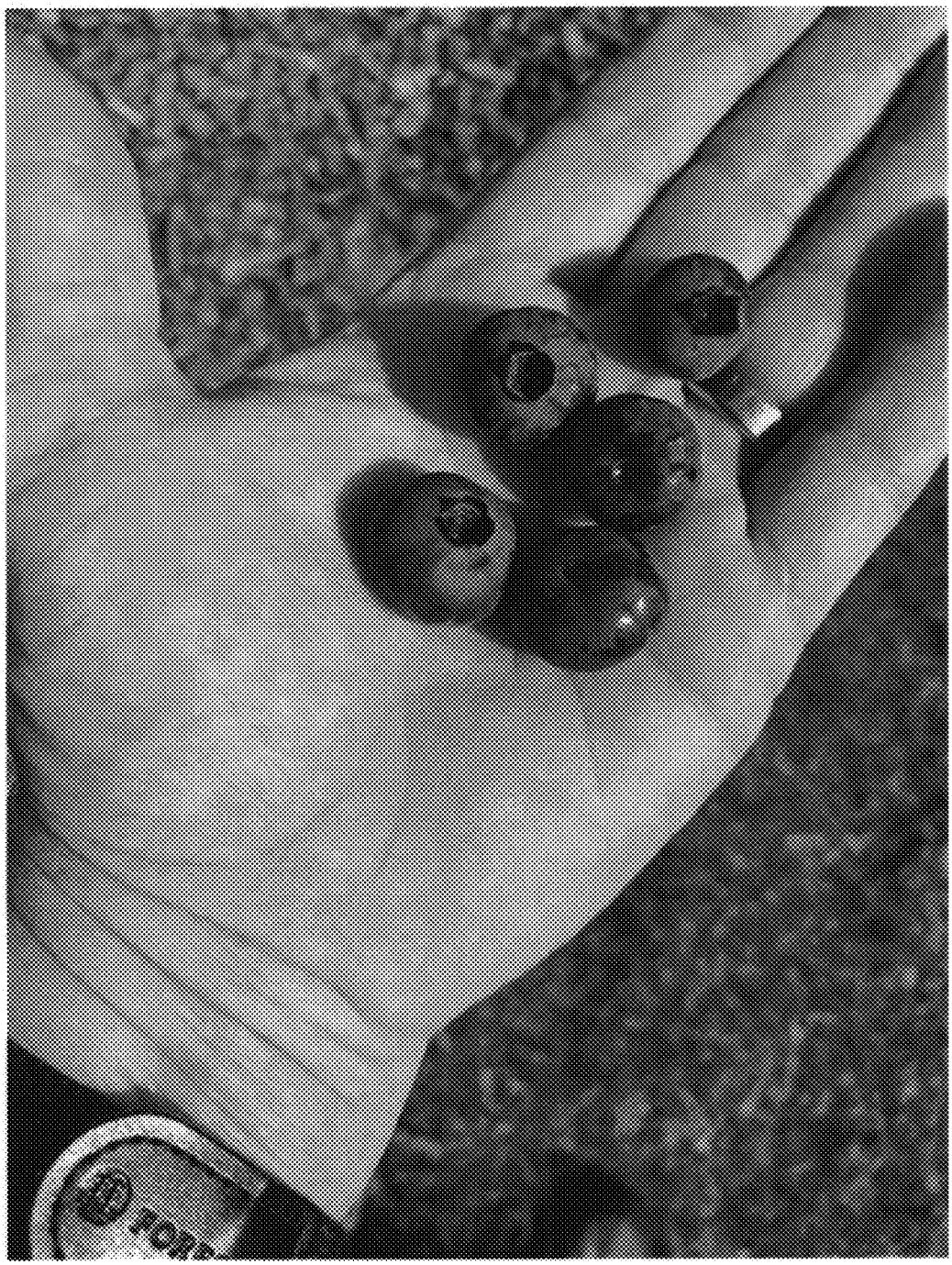

Throughout this specification, color names beginning with a small letter signify that the name of that color, as used in common speech, is aptly descriptive. Color names beginning with a capital letter designate values based upon The R.H.S. Colour Chart, 5$^{th}$ edition published in 2007 by The Royal Horticultural Society, London, England.

The following is a detailed description of the botanical and pomological characteristics of the new variety 'TH-1334'. Where dimensions, sizes, colors, and other characteristics are given, it is to be understood that such characteristics are approximations and averages set forth as accurately as practicable. The descriptions reported herein are largely from three to 6 year old specimen plants grown in Alapaha and Griffin, Ga., with supplemental irrigation.

Plant:

*Size*.—1.3 to 1.6 m tall by 3 years. Plants grown under highly productive soil and fertility conditions have exceeded 1.6 m tall in 4 years. The plant crown, or base, is narrow, typically 15 to 25 cm in diameter. Upper portion of plant canopy reaches 1.2 to 1.5 m in diameter by 3 to 4 years.

*Growth habit*.—Plant is semi-spreading, with 2 to 4 main canes arising from the crown, and multiple branching of shoots from those canes above ground.

*Growth*.—Moderately to highly vigorous.

*Productivity*.—Medium to high crop/yield. Yields of 4 to 8 lbs per plant each year on plants 4 years old or older grown under well-fertilized and irrigated field conditions. Frost protection is required to reach yield potential due to early flowering.

*Cold hardiness*.—Has been grown in Griffin, Ga. and Alapaha, Ga., USDA hardiness zone 8a; similar to other early ripening southern highbush varieties such as 'TH-819' and 'Rebel'.

*Chilling requirement*.—Plants are very low chill, requiring only 50 to 100 hours, more or less, of temperatures at or below 7 C to induce normal leafing and flowering during the spring under conventional dormant production systems. The chill requirement is less than the male parent 'Rebel' (300 to 350 hours of chilling required), and the female parent 'TH-639' (150 to 250 hours of chilling required).

*Leafing*.—Plants tend to break sufficient leaf buds simultaneously with, or shortly after, anthesis.

*Fruiting wood*.—5 to 10 twigs 10 to 15 cm in length, with internode lengths of 15 to 20 mm common.

*Canes*.—Diameter: Main cane base diameter 15 to 30 mm, two-year-old cane diameter 10 to 15 mm, current season wood diameter 3 to 5 mm. Color: RHS Brown N200C for main cane, color transitioning from Yellow Green 145A to Greyed Orange 166C for two-year-old cane, and RHS Yellow Green 145A for current season wood.

*Disease and pest resistance*.—No exceptional disease and pest resistance or susceptibility observed. Typical for early season southern highbush varieties such as 'TH-819' and 'Rebel'.

Foliage:

*Leaf color*.—Healthy mature leaves Top side: Green RHS 137C. Under side: Yellow Green RHS 147C.

*Leaf arrangement*.—Alternate, simple.

*Leaf shape*.—Elliptic.

*Leaf surface*.—Glaucous, upper and lower.

*Leaf margins*.—Nearly entire

*Leaf venation*.—Moderately reticulated.

*Leaf apices*.—Broadly acute.

*Leaf bases*.—Acute.

*Leaf dimensions*.—Length: 60.0 to 70.0 mm. Width: 30.0 to 35.0 mm.

*Petioles*.—Small. Length: Small, 3.0 to 5.0 mm long. Width: 1.5 to 2.0 mm. Color: Yellow Green RHS 145C.

Flowers:

*Date of* 50% *anthesis*.—3-year average February 7 in southeast Georgia.

*Flower shape*.—Urceolate.

*Flower bud number*.—Medium to high, averaging 3 to 6 buds per fruiting shoot.

*Vegetative bud burst*.—Beginning flowering for 'TH-1334' on 1 year old shoots is January 15 to 25 on average. Leaf bud burst occurs nearer 50% flowering, or January 28 to February 5 on average for first leaf buds.

*Flowers per cluster*.—6 to 9.

*Flower fragrance*.—Slight "fresh cut" flower fragrance.

*Corolla tube*.—Color: White NN155C. Length: 10.0 to 11.5 mm. Width: 8.0 to 9.0 mm. Aperture width: 3.0 to 4.0 mm. Anthocyanin coloration: weak to medium anthocyanin coloration in early stages of bud development, but it is absent in nearly open or entirely open corollas.

*Flower peduncle*.—Length: 10.0 to 12.0 mm. Color: Yellow Green RHS 145B.

*Flower pedicle*.—Length: 3.5 to 5.0 mm. Color: Green RHS 138C.

*Calyx* (*with sepals*).—Diameter: 7.5 to 9.0 mm. Color: Green RHS 138C to Green RHS 138B.

*Stamen*.—Length: 7.0 to 8.0 mm. Number per flower: 10. Filament color: Green White RHS 157C.

*Style*.—Length: 10.0 to 11.0 mm. Color: Yellow Green RHS 145B.

*Pistil*.—Length: 12.0 to 13.0 mm. Ovary color (exterior): Green RHS 138B.

*Anther*.—Length: 4.0 to 5.0 mm. Number: 10. Color: Greyed Orange RHS 165B.

*Pollen*.—Abundance: Medium. Color: Yellow White RHS 158B.

*Self-compatibility*.—The cultivar has a moderate degree of self-compatibility.

Fruit:

*Date of* 50% *maturity*.—April 15 in southeast Georgia (3-year average).

*Fruit development period*.—67 days in southeast Georgia.

*Fruit bloom intensity*.—Medium.

*Berry color*.—With wax: Violet Blue RHS 98C. With wax removed: Black RHS 203C.

*Berry surface wax abundance*.—Medium.

*Berry flesh color*.—Green White RHS 157B.

*Berry weight*.—First harvest: 3.0 to 3.8 g. Second harvest: 2.3 to 2.8 g.

*Berry size*.—Height from calyx to scar: 15.0 to 18.0 mm. Diameter: 17.0 to 21.0 mm.

*Berry shape*.—Semi-disk shape, somewhat flat on bottom.

*Fruit stem scar*.—Medium, dry, with little or no tearing upon harvest.

*Calyx*.—Depth medium, 2.0 to 3.0 mm; width medium, 5.0 to 7.0 mm; sepals typically not highly visible, erect when present, <<1 mm.

*Berry firmness*.—Very firm.

*Berry flavor and texture*.—Sweet, slight crispness, smooth texture, mildly (medium) acidic, aromatic.

*Storage quality*.—Very good.

*Suitability for mechanical harvesting*.—Unknown.

*Uses*.—Primarily to be used as fresh fruit for shipping and processing markets.

*Infructescence* (*fruit clusters*).—Medium density or "looseness".

Seed:

*Seed abundance in fruit*.—Medium, with 5 to 10 fully developed seeds per berry.

*Seed color*.—Greyed Orange RHS 165B.

*Seed dry weight*.—55.8 mg per 100 seeds.

*Seed size*.—1.8 to 2.1 mm long.

What is claimed is:

1. A new and distinct variety of southern highbush blueberry plant named 'TH-1334', as illustrated and described herein.

* * * * *